United States Patent [19]

Miyahara et al.

[11] Patent Number: 5,505,836
[45] Date of Patent: *Apr. 9, 1996

[54] SOLID-STATE ION SENSOR

[75] Inventors: Yuji Miyahara, Hitachi; Satoshi Ozawa, Mitaka; Koutarou Yamashita, Katsuta; Yoshio Watanabe, Kokubunji, all of Japan

[73] Assignee: Hitachi, Ltd., Tokyo, Japan

[*] Notice: TThe term of this patent shall not extend beyond the expiration date of Pat. No. 5,413,685.

[21] Appl. No.: 219,259

[22] Filed: Mar. 29, 1994

[30] Foreign Application Priority Data

Jun. 25, 1993 [JP] Japan .................................. 5-154856

[51] Int. Cl.$^6$ .................................................. G01N 27/333
[52] U.S. Cl. ............................................ 204/418; 204/416
[58] Field of Search ...................................... 204/416–420

[56] References Cited

U.S. PATENT DOCUMENTS

| | | | |
|---|---|---|---|
| 3,151,052 | 9/1964 | Arthur et al. | 204/409 |
| 3,498,289 | 3/1970 | Watanabe et al. | 204/420 |
| 3,997,420 | 12/1976 | Buzza | 204/415 |
| 4,020,830 | 5/1977 | Johnson et al. | 204/418 |
| 4,053,381 | 10/1977 | Hamblen et al. | 204/418 |
| 4,214,968 | 7/1980 | Battaglia et al. | 204/418 |
| 4,452,682 | 6/1984 | Takata et al. | 204/416 |
| 4,758,325 | 7/1988 | Kanno et al. | 204/416 |
| 4,776,944 | 10/1988 | Janata et al. | 204/418 |
| 5,413,685 | 5/1995 | Ozawa et al. | 204/418 |

*Primary Examiner*—T. Tung
*Attorney, Agent, or Firm*—Antonelli, Terry, Stout & Kraus

[57] ABSTRACT

The solid-state ion sensor of the present invention comprises an inner electrode comprising a metal and a water-insoluble salt of the metal which covers at least a part of the surface of the metal, an ion-selective membrane selectively responsive to the ion species to be determined, and an intermediate layer comprising a hydrophilic polymeric membrane provided between the inner electrode and the ion-selective membrane. The inner electrode comprises a metal and a halogenide of the metal which covers at least a part of the surface of the metal. In the hydrophilic polymeric membrane is dispersed a hydrophilic electrolyte having halogen ions same as or different from those constituting the halogenide with the weight ratio of the electrolyte and the polymer [(electrolyte) wt. %/(polymer) wt. %] being at least 1/100. A polymeric ion-conductor can be used as the hydrophilic polymeric membrane.

7 Claims, 7 Drawing Sheets

FIG. 1
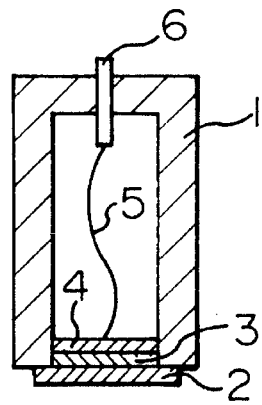
FIG. 2A    FIG. 2B
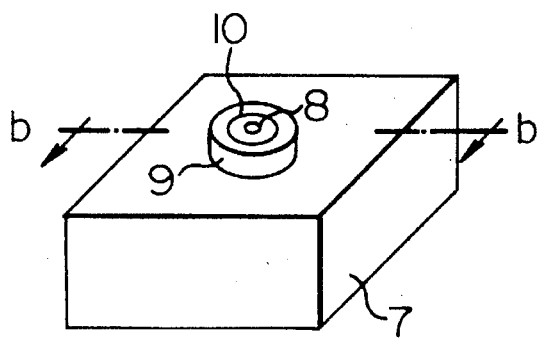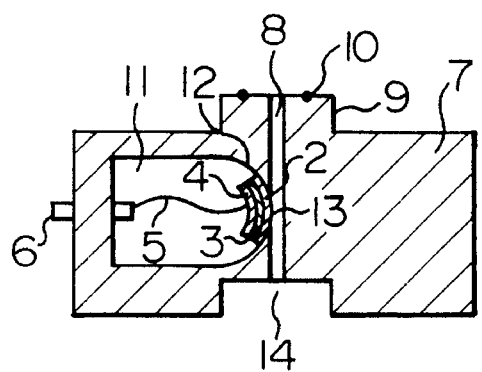
FIG. 3
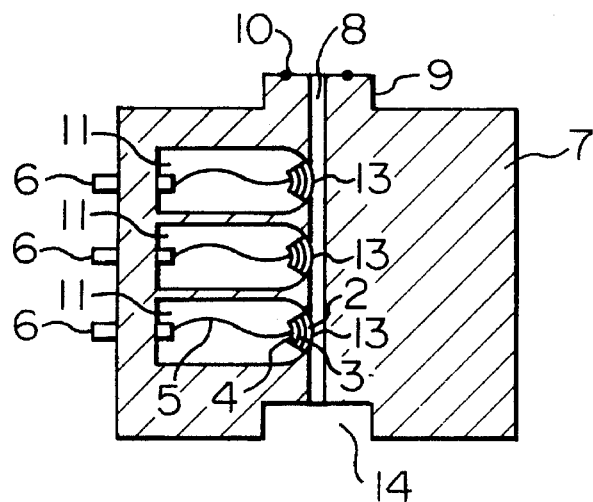

SOLID-STATE ION SENSOR

BACKGROUND OF THE INVENTION

The present invention relates to an ion sensor suitable for being set in apparatuses for analysis of ion species contained in a biological fluid, for example, blood analyzers for medical use, and more particularly to a solid-state ion sensor which does not need special electrolyte solution and which is small in size and can comprise integrated ion sensors for multi-species.

An ion-selective electrode is characterized by selectively determining concentrations of specific ion species in a solution and has been employed in various fields including monitoring for ion concentration, water analysis, etc. Particularly, in the medical field it is applied to quantitative determination of ion species contained in blood or biological fluids such as urine, etc, for example, chloride ions, potassium ions, etc. Since concentrations of specific ion species in a biological fluids are closely related to metabolic reactions of living bodies, diseases for high blood pressure, diseases for kidney, diseases for neurosystem, etc. are diagnosed by determining concentrations of specific ion species.

In the case of a ion-selective electrode, between an activity a of ion species to be determined and an electrode potential E given by the ion-selective electrode, a correlation that the logarithm of activity a is proportional to a change in the electrode potential E is established as shown by the following equation:

$$E = E° + 2.303(RT/Zf) \log a$$

and the activity a of ion species to be determined can be simply calculated from measurements of the electrode potential E. In this way, when an ion-selective electrode is used, the quantitative determination of ion species in a wide range of concentrations becomes possible only by measuring the potential E. In the above equation, R is a gas constant, T is an absolute temperature, Z is a valency, F is a Faraday constant, E° is a standard electrode potential of the system and log is a logarithm.

Generally, as shown in FIG. 15, the conventional ion-selective electrode containing an inner solution comprises sensor body 51 filled with inner solution 52, silver/silver chloride inner electrode 53 being dipped in the inner solution 52, ion-selective membrane 54 being fixed at the center of the sensor body 51 along biological fluid channel 55. In the conventional ion-selective electrode, an aqueous electrolyte solution or an agar gel containing a supporting electrolyte is used as the inner solution 52 which serves to conduct electricity between the ion-selective membrane 54 and the inner electrode 53 ("Analytical Chemistry", Vol.52 No.4 pp.692–700 (1980)).

A small-sized potassium ion sensor manufactured by photolithographic process is described in "Sensors and Actuators", Vol.11 (1987), pp.23–36. This sensor is made by forming a conductive electrode such as of a metal on a silicon chip and providing an ion-selective membrane on the conductive electrode.

Furthermore, an ion-selective electrode is known which has a layer comprising a dry residue of a hydrophilic material provided between an electrode comprising a metal and its water-insoluble salt and an ion-selective membrane (U.S. Pat. No. 4,053,381).

In the above-mentioned conventional solid-state ion sensor described in "Sensors and Actuators", Vol.11 (1987), pp.23–36, the ion-selective membrane is directly provided on the electrode. Therefore, the sensor has the problem that exchange of charges between the ion-selective membrane and the electrode is not efficiently conducted and thermodynamic equilibrium is not established and thus, the potential drift is great. Moreover, since there is no electrolyte between the ion-selective membrane and the electrode, this solid-state ion sensor greatly differs in the electrode potential from the conventional ion-selective electrode having an electrolyte (inner solution) and the measuring circuit for conventional ion sensors cannot be used and a special measuring circuit is needed.

Furthermore, the conventional ion-selective electrode in which an agar gel containing a supporting electrolyte is used as the inner solution which serves to conduct electricity between the ion-selective membrane and the inner electrode has the problem that the stability decreases when used for a prolonged time due to the gradual gasification of water molecules contained in the agar gel.

SUMMARY OF THE INVENTION

An object of the present invention is to provide a solid-state ion sensor high in stability which is free from the problems experienced with the above-mentioned conventional solid-state ion sensors and the conventional ion-selective electrodes having agar gel containing a supporting electrolyte. Another object of the present invention is to provide a solid-state ion sensor which shows an electrode potential equivalent to that of the conventional ion-selective electrode having an electrolyte, has no electrolyte as a constitutive element and can be used stably for a prolonged time.

The present invention is characterized by providing an intermediate layer between an ion-selective membrane selectively responsive to the ion species to be determined and a metal/metal halogenide inner electrode. This intermediate layer (the first type intermediate layer) is characterized by comprising a hydrophilic polymeric membrane in which a hydrophilic electrolyte containing the same halogen ions as constituting the halogenide or a hydrophilic electrolyte containing ions different from the ion species to be determined or different from the halogen ions constituting the halogenide is dissolved or dispersed, the weight ratio of the hydrophilic electrolyte and the hydrophilic polymer being at least 1/100. The present invention is further characterized by providing an intermediate layer between a water-permeable ion-selective membrane selectively responsive to the ion species to be determined and a metal/metal halogenide inner electrode, the intermediate layer comprising a hydrophilic polymeric membrane which absorbs and retains water, a hydrophilic electrolyte in an amount larger than the saturation dissolution amount based on the amount of water retained in the polymeric membrane being dispersed in the polymeric membrane.

The ion-selective membrane can be formed of a matrix, a plasticizer and an ion-selective material, if necessary, with additives. Polyvinyl chloride or silicone rubber can be used as the matrix. The plasticizer can be selected from the group consisting of dioctyl adipate (DOA), dioctyl sebacate (DOS), tri(2-ethylhexyl) trimellitate (TOTM), o-nitrophenyloctyl ether (o-NPOE), tris(2-ethylhexyl) phsphate (TEHP) and n-tetradecyl alcohol (n-TDA). The ion-selective material can be selected, depending on the purposes, from the group consisting of valinomicin, [bis(12-crown-4)methyl] methyldodecylmalonic acid, quaternary ammonium salts, etc. As the additives, there may be used potassium tetraphenylborate or sodium tetraphenylborate. The matrix, plasticizer and ion-selective material and, if necessary, the additives are combined so that an optimal composition can be obtained, taking into consideration the accuracy and stability of the sensor and are homogeneously dissolved in a volatile organic solvent such as tetrahydrofuran. The solution is spread on a substrate and then the solvent is evaporated to obtain an ion-selective membrane.

As the metal and the halogenide of the metal for the inner electrode, there may be used, for example, Ag-AgCl, Hg-HgCl2 and Ag-AgBr.

The hydrophilic polymeric membrane which constitutes the intermediate layer (the first type intermediate layer) can be a membrane of a polymer selected from the group consisting of polyvinyl alcohol, agarose, polyacrylamide, and polyethylene oxide.

(i) polyalkylene oxides (1):

wherein n is an integer of 1–5 and m indicates a degree of polymerization of 1000–100,000. When n is 2 or 3, the polyalkylene oxide is polyethylene oxide or polypropylene oxide, respectively.

(ii) polymers having oxide chain (2):

wherein R is a hydrogen atom or an alkyl group, l indicates a degree of polymerization of 100–1000, n is an integer of 1–5, and m indicates a degree of polymerization of 1000–100,000. The carbon number of the alkyl group represented by R is not considered limited, but the carbon number is preferably 1–4.

The hydrophilic electrolyte can be selected from the group consisting of halogenides of alkali metals such as sodium chloride, sodium bromide, sodium iodide, potassium chloride, potassium bromide and potassium iodide and halogenides, hydrogencarbonates, acetates, nitrates, sulfates and phosphates of alkali metals and alkaline earth metals.

An ion-concentration analyzer which can simply determine the ion concentration in biological fluids such as blood and urine, specifically K, Na or Cl ion concentration and thus is useful for diagnosis of diseases can be constructed by providing the solid-state ion sensor of the present invention in in a sample channel of a small diameter formed of polyvinyl chloride in such a state as exposed to the channel or by connecting it to a gate electrode of a field effect transistor.

When the ion-selective membrane of the solid-state sensor of the present invention is allowed to contact with a standard solution of a given composition for a given period to subject it to conditioning and thus, the solid-state sensor is made to be in an operable state, water in the standard solution diffuses into the intermediate hydrophilic polymeric membrane through the ion-selective membrane. The polymeric membrane which constitutes the intermediate layer is hydrophilic and can retain water, and the electrolyte dispersed or dissolved in the polymeric membrane is dissociated by the action of the water.

In case the hydrophilic electrolyte comprising cations to be determined and halogen ions is dispersed in the polymeric membrane which constitutes the intermediate layer and the metal halogenide which constitutes the inner electrode contains the same halogen ions as above, the dissociated halogen ions equilibrate with the metal halogenide of the inner electrode. Furthermore, since the ions to be determined form a complex with the ion-selective material in the ion-selective membrane, an equilibrium is established between the ions and the ion-selective membrane.

When a hydrophilic electrolyte comprising the ions to be determined or ions other than the halogen ions of the inner electrode is dispersed in the polymeric membrane which constitutes the intermediate layer and a metal halogenide is used for the inner electrode, the dissociated anions other than the halogen ions of the inner electrode equilibrate with the metal halogenide constituting the inner electrode at a specific selectivity to give a potential in correspondence to the selectivity coefficient. The dissociated cations other than the ions to be determined are taken in the ion-selective membrane with a specific selectivity to equilibrate with the ion-selective membrane to give a potential in correspondence to the selectivity coefficient. If the composition and the concentration of the test solution are fixed, since the electrode potential in the solid-state ion sensor is a sum of the potential of the metal halogenide given by the anions in the polymeric membrane and the potential of the ion-selective membrane given by the cations, the degree of selectivity is changed by choosing the kinds of the cations and the anions and thus the electrode potential of the solid-state ion sensor can be changed.

As the intermediate layer provided between the ion-selective membrane and the inner electrode, use of the first type intermediate layer having the above construction is explained hereabove. However, the object of the present invention can be similarly attained by using a hydrophilic polymeric ion-conductor as the intermediate layer.

Use of the hydrophilic polymeric ion-conductor as the intermediate layer (the second type intermediate layer) will be explained below.

One of the main components of the second type intermediate layer is a polymeric ion-conductor having hydrophilicity. This is not limitative and any known polymeric ion-conductors can be used as long as they are hydrophilic. The hydrophilic polymeric ion-conductor has an alkali metal salt as a constitutive element and an alkali metal salt is able to dissociate and ionize, and the hydrophilic polymeric ion-conductor exhibits conductivity. Furthermore, as the second type intermediate layer, there may be used various hydrophilic polymeric ion-conductors enumerated below in which the hydrophilic electrolytes usable in the first type intermediate layer or various (such as salts of tetraphenylboric acid, salts of tetraphenylboric acid derivatives, salts of tetraalkylboric acids and salts of tetraalkylboric acid derivatives) are dispersed in an amount of 20–50% by weight. That is, the second type intermediate layer may comprise the polymeric ion-conductor alone or may comprise 50–80% by weight of the polymeric ion-conductor and 20–50% by weight of the salt.

Examples of the hydrophilic polymeric ion-conductors used suitably in the present invention are shown below by the formulas.

(iii) Polymers having carboxylate (3):

wherein R is a hydrogen atom or an alkyl group and l indicates a degree of polymerization of 100–1,000. The carbon number of the alkyl group represented by R is unlimited, but the carbon number is preferably 1–4. X is a cation of an alkali metal. When R is a hydrogen atom or a methyl group, the polymer is a salt of a polyacrylate or a polymethacrylate respectively.

(iv) Polymers having sulfonic acid salt (4):

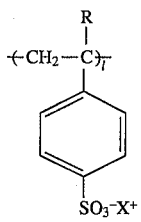
(4)

wherein R is a hydrogen atom or an alkyl group and l which is a degree of polymerization is 100–1,000. The carbon number of the alkyl group represented by R is unlimited, but it is preferably 1–4. X is a cation of an alkali metal. When R is a hydrogen atom, the polymer is a polystyrenesulfonic acid salt.

(v) Natural polymers having carboxylate (5) and (6):

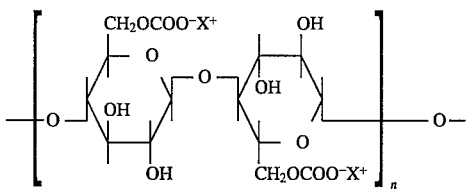
(5)

The polymers are cellbioses in which a carboxylate is substituted for the hydroxyl group of the hydroxymethyl group. X is a cation of an alkali metal and n which is a degree of polymerization is 1000–10000.

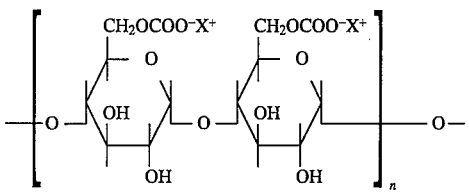
(6)

The polymers are maltoses in which a carboxylate is substituted for the hydroxyl group of the hydroxymethyl group. X is a cation of an alkali metal and n which is a degree of polymerization is 10–1000.

When the second type intermediate layer provided between the ion-selective membrane and the inner electrode comprises the polymeric ion-conductor having an alkali metal salt as a constitutive element, the alkali metal salt is dissociated and ionized and the salt constituted by the polymer per se is ionized, whereby the polymer shows excellent conductivity. The polymer further shows conductivity based on the segment motion of the polymer. The above-mentioned polymeric conductors are water-soluble and superior in processability. Besides, since they do not contain water molecules, being different from the conventional agar gels, deterioration of electrode performance caused by evaporation of water molecules occurs with difficulty. As a result, stability and accuracy required for ion-selective electrodes are improved and long-term use of the sensor becomes possible.

BRIEF DESCRIPTION OF THE DRAWINGS

FIG. 1 is a sectional view of the solid-state ion sensor of Example 1 of the present invention.

FIGS. 2A and 2B are an oblique view and a sectional view of the solid-state ion sensor of Example 2 of the present invention, respectively.

FIGS. 3 and 4 are sectional views of the solid-state sensors of Examples 3 and 4 of the present invention, respectively.

DETAILED DESCRIPTION OF THE INVENTION

Figure 4:
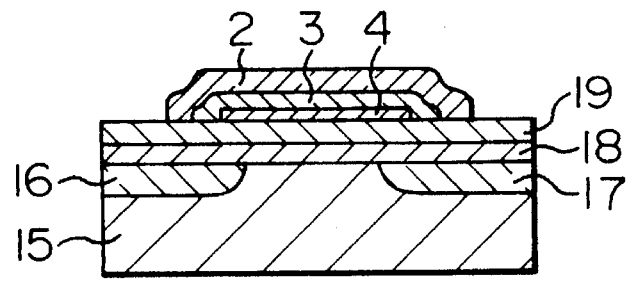

The following examples are illustrative of the present invention. First, solid-state ion sensors in which the first type intermediate layer is used will be explained.

EXAMPLE 1

FIG. 1 shows the first example of the solid-state ion sensor according to the present invention. An ion-selective membrane 2 was allowed to adhere to one end of a cylindrical polyvinyl chloride sensor body 1, a hydrophilic polymeric membrane 3 was provided in contact with the ion-selective membrane, and a metal/metal halogenide inner electrode 4 was provided so that the metal halogenide contacted with the hydrophilic polymeric membrane. One end of a lead wire 5 for taking out signals was connected to the metal portion of the metal/metal halogenide inner electrode 4 and another end of the lead wire was connected to a terminal 6 for connecting with an external measuring circuit.

When the ion-selective membrane is subjected to conditioning by contacting it with a standard solution containing ion species in the known concentration or a sample solution, water is taken in the hydrophilic polymeric membrane to dissociate the hydrophilic electrolyte in the hydrophilic polymeric membrane. Due to the action of the dissociated electrolyte, an equilibrium is established between the hydrophilic polymeric membrane and both the phases of the ion-selective membrane phase and the metal halogenide phase and the solid-state ion sensor shows a stable potential. Furthermore, by changing the kind of the hydrophilic electrolyte, the potential at the interfaces of ion-selective membrane/hydrophilic polymeric membrane and hydrophilic polymeric membrane/metal halogenide can be changed and hence the electrode potential of the solid-state ion sensor can be set at a given value.

EXAMPLE 2

FIGS. 2A and 2B show the second example of the solid-state ion sensor of the present invention. FIG. 2A is an oblique view of the flow cell type solid-state ion sensor of this example. A through-hole 8 of 1 mm in diameter was made between opposite faces of a rectangular parallelopiped polyvinyl chloride sensor body 7. This through-hole is a channel through which a sample solution or a standard solution containing ion species to be determined in a known concentration is flowed. When a plurality of the sensor bodies are stacked and used, for easy registration of the channels, a columnar convex part 9 is provided at one of the faces between which the through-hole was made. An O-ring 10 was provided on the upper surface of the convex part 9 for preventing leakage of the solution.

FIG. 2B is a sectional view of the solid-state ion sensor shown in FIG. 2A, taken along line b-b' of FIG. 2A. A vacant space 11 was provided in a part of the sensor body 7. The inner bended plane 12 of the vacant space 11 intersected the channel 8 and an oval small hole 13 of 0.5 mm in shorter diameter and 1.5–2 mm in longer diameter was formed at the side wall of the channel. Ion-selective membrane 2 was formed along the bended plane 12 so as to completely cover the small hole 13 and protrude in the convex form towards the channel. Hydrophilic polymeric membrane 3 and metal/ metal halogenide inner electrode 4 were laminated on the face of the ion-selective membrane which was opposite to the face of channel side and the metal part of the inner electrode 4 was connected to terminal 6 for connection with the external measuring circuit by lead wire 5. Furthermore, when a plurality of the sensor bodies 7 were stacked and used, for easy registration of the channel 8, a recessed part 14 fitting to the columnar convex part 9 was provided at the face of the sensor body opposite to the face provided with the convex part.

According to this construction, the ion concentration can be continuously determined by successively introducing the sample solution or the standard solution into the channel. Furthermore, by protruding the ion-selective membrane in the convex form towards the channel, the sample is not retained in the vicinity of the ion-selective membrane and a rapid response can be obtained. Furthermore, since cleaning can be easily conducted, even when a plurality of samples are analyzed, the influence caused by the previously analyzed sample can be completely prevented.

EXAMPLE 3

FIG. 3 shows the third example of the solid-state ion sensor according to the present invention. The construction corresponds to that of the solid-state ion sensor of Example 2 where three independent vacant spaces 11 were provided in the sensor body 7 and ion-selective membranes 2 responsive to different ion species were formed in the convex form at the small holes 13 provided at the contact points of the vacant space 11 and the channel 8. The materials and the positions of the members in the respective vacant spaces were the same as in Example 2.

According to this construction, three solid-state ion sensors can be handled all together and besides, three kinds of ion species can be simultaneously determined. Thus, this is convenient.

EXAMPLE 4

FIG. 4 shows the fourth example of the solid-state sensor of the present invention. This example illustrates a field effect transistor in which source 16 and drain 17 were provided on silicon substrate 15 and the surface of the silicon substrate was covered with insulation films of silicon dioxide 18 and silicon nitride 19, and on the surface of the silicon nitride film between the source 16 and the drain 17 was formed the metal/metal halogenide inner electrode 4 as a gate electrode and a potential detecting electrode in the ion-selective membrane. Hydrophilic polymeric membrane 3 and ion-selective membrane 2 were laminated on the metal/metal halogenide inner electrode 4.

According to this example, since the solid-state ion sensor can be manufactured using semiconductor techniques, miniaturization and integration of sensors are possible and the sensors are suitable for mass production and thus, cheap sensors can be provided.

EXAMPLE 5

Figure 5A:
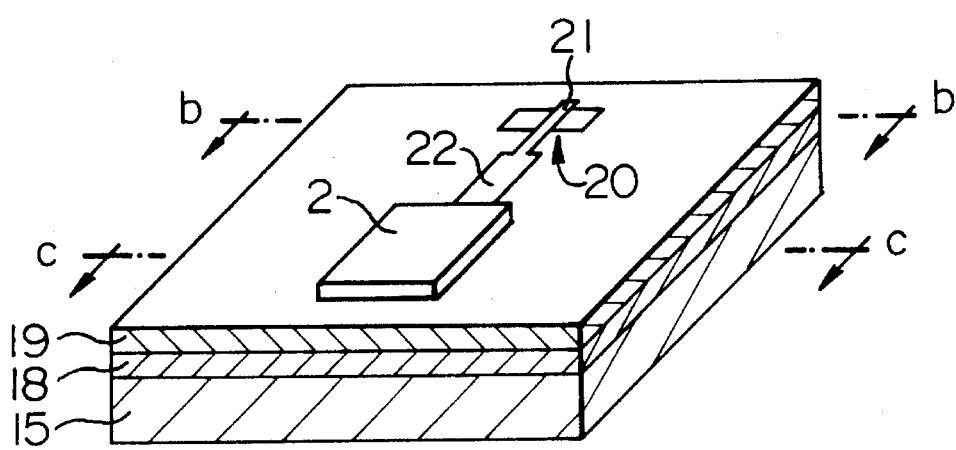
FIGS. 5A, 5B and 5C are an oblique view, and sectional views which show the first and second parts of the solid-state ion sensor of Example 5 of the present invention, respectively.
Figure 5B:
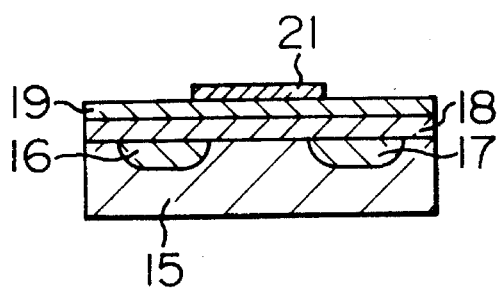
Figure 5C:
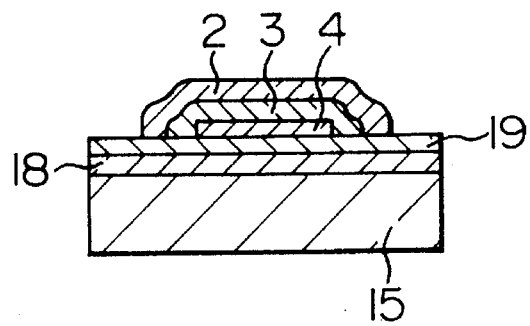

FIGS. 5A, 5B and 5C show the fifth example of the solid-state sensor of the present invention. FIG. 5A is an oblique view of the sensor. Insulation film 18 of silicon dioxide and insulation film 19 of silicon nitride were formed on the surface of silicon substrate 15, a metal/metal halogenide inner electrode, a hydrophilic polymeric membrane and ion-selective membrane 2 were laminated on the silicon nitride film 19. Field effect transistor 20 was formed on the same silicon substrate and the metal was connected to the gate electrode 21 of the field effect transistor 20 by interconnect 22. As the material of the interconnect, silver, aluminum, polysilicon made conductive by doping with P or B or the like can be used. Especially, when a polysilicon is used and the insulation films comprising silicon dioxide and silicon nitride are formed thereon, the interconnect portion can be protected from the sample solution and this is effective for ensuring the stability of sensors.

FIG. 5B is a sectional view of the sensor shown in FIG. 5A, taken along line b-b' to show the first part of the sensor. Source 16 and drain 17 were provided on a part of the surface of silicon substrate 15 and the surface of the silicon substrate were covered with insulation films of silicon dioxide 18 and silicon nitride 19. Gate electrode 21 was formed on the surface of silicon nitride between the source 16 and the drain 17. As the material of the gate electrode, silver, aluminum, conductive polysilicon, etc. can be used.

FIG. 5C is a sectional view of the sensor shown in FIG. 5A, taken along line c-c' to show the second part of the sensor. The surface of the silicon substrate 15 was covered with the insulation films of silicon dioxide 18 and silicon nitride 19. The metal/metal halogenide inner electrode 4 was formed on silicon nitride, the hydrophilic polymeric membrane 3 was provided so that it covered the whole electrode, and furthermore, ion-selective membrane 2 was laminated so that it covered the whole hydrophilic polymeric membrane. According to this example, since the field effect transistor and the ion-selective membrane part were separated, there are such merits that with maintaining the features of the fourth example, further the packaging is easy and the field effect transistor can be protected from the solution with ease.

Moreover, the solid-state ion sensor of the present invention can also be formed on the substrate of polyvinyl chloride. In this case, signals from the sensor electrode are inputted to the external measuring circuit through the lead wire.

EXAMPLE 6

Figure 6:
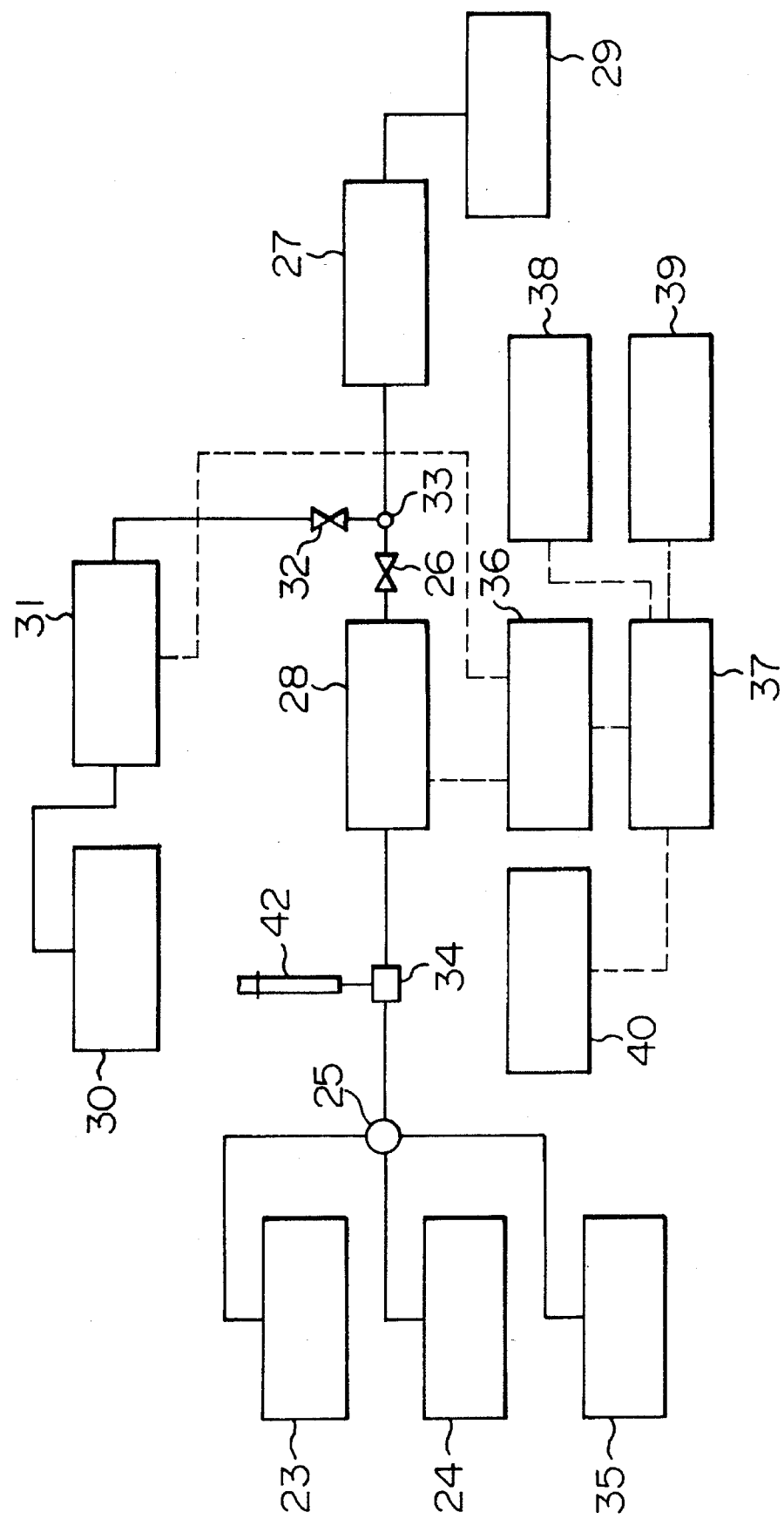
FIG. 6 is a diagram of an analyzer in which the solid-state ion sensor of the present invention is used.

FIG. 6 shows a diagram of the ion-concentration analyzer in which the solid-state ion sensor of the present invention is set. In FIG. 6, the route shown by the solid line indicates the channel and the broken line indicates the signal line.

Standard solution 23 for calibration containing ion species of known concentration and standard solution 24 are introduced into the solid-state ion sensor 28 of the present invention by peristaric pump 27 through change-over valve 25 and on-off valve 26 and discharged to bottle 29 for waste solution. Inner solution 30 for reference electrode joins with the channel downstream from the on-off valve 26 by the peristaric pump 27 through reference electrode 31 and on-off valve 32 to form liquid-liquid junction 33. Simply, the sample such as blood is introduced into the channel by injecting into sample injector 34 formed of silicone rubber, etc. by syringe 42. After analyzing the sample, cleaning solution 35 is introduced into the channel to clean the channel for the next analysis. The potential difference between the solid-state ion sensor 28 and the reference electrode 31 is measured and processing such as conversion to concentration is carried out at data-processor 37, and sample information and results of measurement are displayed at display 38 and recorded at recorder or printer 39. If necessary, they are memorized in memory 40. According to the ion-concentration analyzer of this construction, ion concentration in the sample can be continuously and rapidly determined.

Stability of the solid-state ion sensors of the above examples will be explained below.

Figure 7:
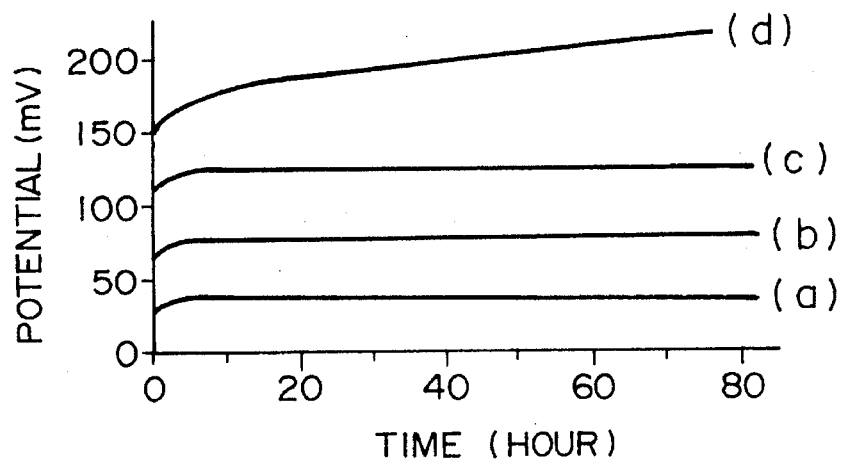
FIGS. 7, 8 and 9 are graphs which show the potential stability of sodium ion sensor, potassium ion sensor and chloride ion sensor of the present invention, respectively.
Figure 8:
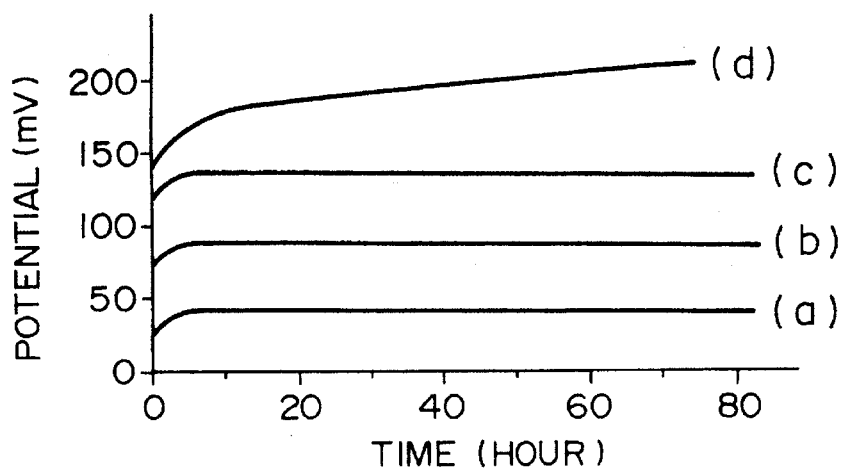
Figure 9:
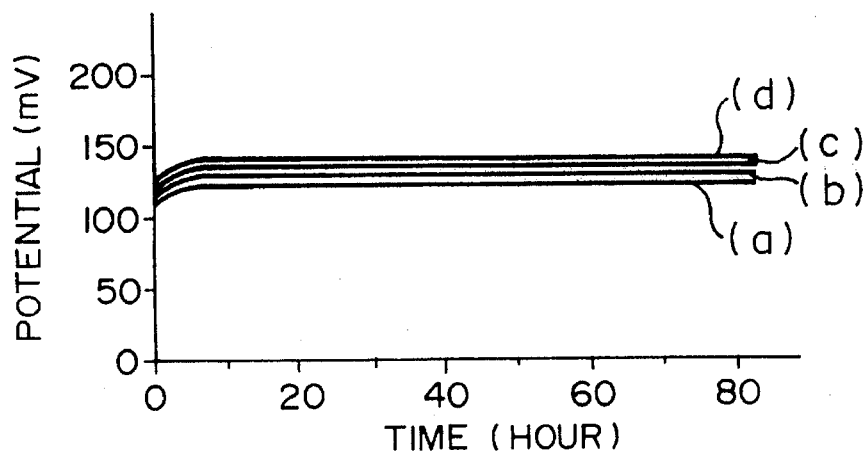

FIGS. 7–9 are graphs which show change in the potential with time measured by the analyzer of FIG. 6 in which the solid-state ion sensor of FIG. 2 of the present invention was used. A silver/silver chloride electrode was used as the metal/metal halogenide inner electrode of the solid-state ion sensor and polyvinyl alcohol was used as the hydrophilic polymer.

EXAMPLE 7

FIG. 7 shows the results obtained when sodium chloride was used as the hydrophilic electrolyte and a sodium ion-selective membrane comprising polyvinyl chloride, DOA, [bis(12-crown-4)methyl]methyldodecylmalonic acid and sodium tetraphenylborate was used as the ion-selective membrane. Sodium chloride was dispersed in polyvinyl alcohol to prepare an intermediate layer membrane. In FIG. 7, curves (a)–(d) show the change in potential of the sensors in which the weight ratio of polyvinyl alcohol:sodium chloride was (a) 1:1, (b) 10:1, (c) 100:1 and (d) 1000:1, respectively.

Thus, the potential of the sensors in which the weight ratio of polyvinyl alcohol:sodium chloride was 1:1–100:1 was stable while the potential of the sensor in which the weight ratio was 1000:1 showed a great drift.

It is considered that in the case of the weight ratio of sodium chloride and polyvinyl alcohol [(NaCl) wt. %/(PVA) wt. %] being higher than 1/100, even when water is taken into polyvinyl alcohol through the ion-selective membrane, the concentration of sodium chloride is in nearly saturated state and there occurs no change in the concentration with time. Accordingly, due to the action of water taken into polyvinyl alcohol, sodium chloride is dissociated to produce sodium ion and chloride ion, and the sodium ion equilibrates with the ion-selective membrane and the chloride ion equilibrates with silver chloride. As a result, the potential is stable. On the other hand, it is considered that in the case of the amount of sodium chloride in polyvinyl alcohol being small, when water is taken into polyvinyl alcohol, the concentration of sodium chloride changes with time and equilibrium is not established at the interfaces of ion-selective membrane/polyvinyl alcohol and polyvinyl alcohol/silver chloride, and therefore, the potential of the sensor is not stabilized.

EXAMPLE 8

FIG. 8 shows the results obtained when potassium chloride was used as the hydrophilic electrolyte and a potassium ion-selective membrane comprising polyvinyl chloride, DOA, valinomicin and potassium tetraphenylborate was used as the ion-selective membrane. Potassium chloride was dispersed in polyvinyl alcohol to prepare an intermediate layer membrane. In FIG. 8, curves (a)–(d) show the change in potential of the sensors in which the weight ratio of polyvinyl alcohol: potassium chloride was (a) 1:1, (b) 10:1, (c) 100:1 and (d) 1000:1, respectively.

Thus, the potential of the sensors in which the weight ratio of polyvinyl alcohol:potassium chloride was 1:1–100:1 was stable while the potential of the sensor in which the weight ratio was 1000:1 showed a great drift. This is for the same reasons as in the case of the above-mentioned sodium ion sensor.

EXAMPLE 9

FIG. 9 shows the results obtained when sodium chloride was used as the hydrophilic electrolyte and a chloride ion-selective membrane comprising polyvinyl chloride, NPOE, n-TDA and a quaternary ammonium salt was used as the ion-selective membrane. Sodium chloride was dispersed in polyvinyl alcohol to prepare an intermediate layer membrane. In FIG. 9, curves (a)–(d) show the change in potential of the sensors in which the weight ratio of polyvinyl alcohol:sodium chloride was (a) 1:1, (b) 10:1, (c) 100:1 and (d) 1000:1, respectively.

Being different from the stability and potential of the sodium ion sensor and the potassium ion sensor, those of the chloride ion sensor do not rely so much on the weight ratio of polyvinyl alcohol and sodium chloride. When concentration of the electrolyte in the intermediate layer changes in the chloride ion sensor, the potential of silver/silver chloride electrode changes depending on the concentration of chloride ion and simultaneously the potential at the interface of chloride ion-selective membrane/intermediate layer also changes in such a manner that it just denies the change of potential which occurs at the silver/silver chloride electrode. That is, the change in potential at the interface of ion-selective membrane/intermediate layer and the change in potential at the interface of intermediate layer/silver chloride are nearly the same in quantity and are opposite in direction (polarity) and they are offset each other. Therefore, apparently, the potential of the sensor does not rely on the weight ratio of polyvinyl alcohol and sodium chloride and is nearly constant. However, considering the efficiency in production of sensors, it is preferable that the intermediate layer of the chloride ion sensor also has the same composition as the sodium ion sensor and the potassium ion sensor and considering the electric conductivity of the intermediate layer, the higher concentration of the electrolyte is desired.

From the above, it can be seen that the weight ratio of sodium chloride or potassium chloride and polyvinyl alcohol [(NaCl or KCl) wt. %/(PVA) wt. %] must be higher than 1/100 for obtaining a stable sodium or potassium solid-state ion sensor. Furthermore, the electrode potential of solid-state ion sensors relies on the weight ratio of sodium chloride as an electrolyte and polyvinyl alcohol and increases with decrease of the weight ratio.

EXAMPLE 10

The solid-state ion sensor of the present invention shown in FIG. 2 was set in the analyzer shown in FIG. 6 and the electrode potential was measured with changing the kind of the hydrophilic electrolyte. The results are shown in Table 1.

A silver/silver chloride electrode was used as the metal/metal halogenide inner electrode. Polyvinyl alcohol was used as the hydrophilic polymer, and a sodium ion-selective membrane comprising polyvinyl chloride, DOA, [bis(12-crown-4)methyl]methyldodecylmalonic acid and sodium tetraphenylborate was used as the ion-selective membrane. In Table 1, the lateral column shows the kinds of hydrophilic electrolytes dispersed in polyvinyl alcohol.

TABLE 1

| Kind of salt | NaCl | $KHCO_3$ | $CH_3COOK$ |
|---|---|---|---|
| Potential (mV) | −165 | 30 | 45 |

When sodium chloride (NaCl) was used as the electrolyte, the potential of the solid-state ion sensor was −165 mV while when potassium hydrogencarbonate ($KHCO_3$) and potassium acetate ($CH_3COOK$) were used, the potentials were 30 mV and 45 mV, respectively. Thus, the electrode potential can be changed by changing the kind of the salt.

This is because the anion such as $HCO_3$ ion or $CH_3COO$ ion dissociated by the action of water taken into polyvinyl alcohol equilibrates with silver chloride at a fixed selectivity and gives a potential in correspondence to the selectivity coefficient and the cation such as dissociated potassium ion is taken into the ion-selective membrane at a fixed selectivity and equilibrates with the ion-selective membrane and gives a potential in correspondence to the selectivity coefficient. Accordingly, the electrode potential can be changed by the combination of anion and cation of the electrolyte used, and a solid-state ion sensor easy to use can be provided.

EXAMPLE 11

The solid-state ion sensor of the present invention shown in FIG. 2 was set in the analyzer shown in FIG. 6. The correlation between the results of determination according to the solid-state ion sensor of the present invention and the results of determination according to the standard methods, namely, by flame photometry for sodium ion and potassium ion and by coulometric titration for chloride ion was shown in FIG. 10.

A silver/silver chloride electrode was used as the metal/metal halogenide inner electrode of the solid-state ion sensor. Polyvinyl alcohol was used as the hydrophilic polymer and sodium chloride or potassium chloride was used as the hydrophilic electrolyte to be dispersed in polyvinyl alcohol. Polyvinyl chloride, DOA, [bis(12-crown-4)methyl]methyldodecylmalonic acid and sodium tetraphenylborate were used for the sodium ion-selective membrane. Polyvinyl chloride, DOA, valinomicin and potassium tetraphenylborate were used for the potassium ion-selective membrane. Polyvinyl chloride, o-NPOE, n-TDA and quaternary ammonium salt were used for the chloride ion-selective membrane. Human serum was used as the sample.

Figure 10A:
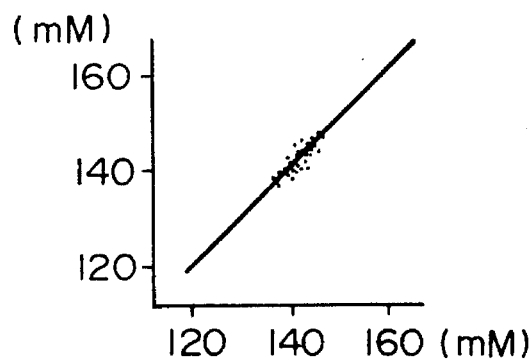
FIGS. 10A, 10B and 10C are graphs which show correlation between the results of determination by the solid-state ion sensors of the present invention and the results of determination by the standard method for the sodium ion sensor, the potassium ion sensor and the chloride ion sensor, respectively.
Figure 10B:
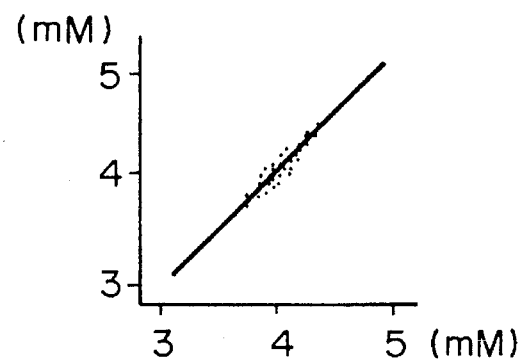
Figure 10C:
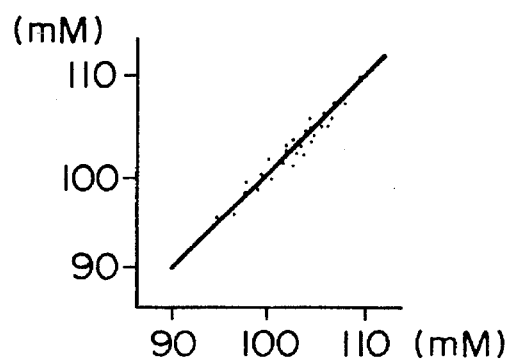

FIG. 10A, FIG. 10B and FIG. 10C show the comparative results on the sodium ion sensor, the potassium ion sensor and the chloride ion sensor, respectively. In these Figures, the abscissa axis indicates the determined values (ion concentration, mM) according to the standard method and the ordinate axis indicates the determined values (ion concentration, mM) according to the solid-state ion sensor of the present invention.

From these Figures, the correlation coefficient (r) was 0.9 or higher for all of the sensors and the standard deviation from the linear regression (Syx) was 1.1 for the sodium ion sensor, 0.04 for the potassium ion sensor and 0.9 for the chloride ion sensor which were all satisfactory values.

As mentioned above, according to the present invention, solid-state ion sensors which need no inner electrolyte solution and are excellent in stability can be produced. Therefore, ion sensors free from the defects caused by evaporation of the inner electrolyte solution can be provided. Furthermore, since the solid-state ion sensors of the present invention show the electrode potential equal to that of the ion-selective electrode containing inner electrolyte solution, ion sensors easy to use can be provided. Furthermore, since the solid-state ion sensors of the present invention can be manufactured by the technique for making semi-conductors, miniaturization and integration are possible and cheap ion sensors can be provided.

Next, solid-state ion sensors having the second type intermediate layer will be explained.

EXAMPLE 12

Figure 11:
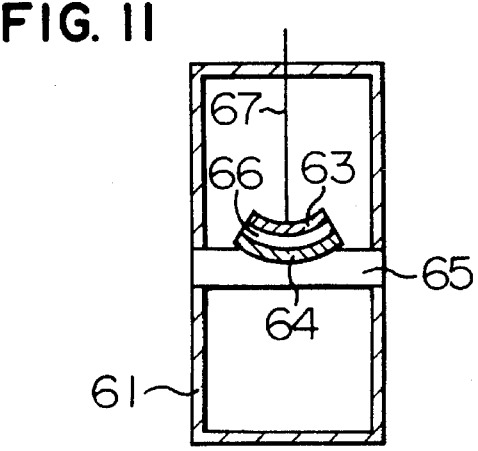
FIG. 11 is a sectional view of the solid-state ion sensor of Example 12 of the present invention.

FIG. 11 is a sectional view of the solid-state ion sensor to which the present invention was applied. Ion-selective membrane 64 was fixed at the center of sensor body 61 along channel 65 for the biological fluid. Intermediate layer 66 comprising a polymeric ion-conductor was interposed between ion-selective membrane 64 and silver/silver halide inner electrode 63. The number 67 indicates a lead wire. The content of the polymeric ion-conductor is suitably 50–80% by weight from the point of processability. The thickness of the intermediate layer is desirably 20 μm or more from the point of strength as an intermediate layer and at most 150 μm in order that the time for which ions migrate through the intermediate layer is within a practical range. The inner electrode 63 may have the construction of metal/metal halogenide comprising a metal and a halogenide of the metal which covers at least a part of the surface of the metal.

The silver/silver tetraphenylborate inner electrode used in the following Examples 13–18 was prepared in the following manner. Electrodeposition was carried out using a silver plate (10 mm×10 mm with 0.2 mm thick) pretreated with conc. nitric acid as an anode and a platinum wire (0.5 mm in diameter×50 mm) as a cathode in a methyl alcoholic solution of potassium tetraphenylborate (1 mM) by application of a voltage of about 1.5 V for about 30 minutes. After completion of the electrodeposition, the electrode was washed with water and dried to obtain a silver/silver tetraphenylborate inner solid electrode.

The composition of the potassium ion-selective membrane used in the following Examples 13 –18 and Comparative Example is shown below.

Composition of the potassium ion-selective membrane:

| Valinomicin | 4.7% by weight |
|---|---|
| Polyvinyl chloride | 94.8% by weight |
| Didodecyl phthalate | 0.5% by weight |

EXAMPLE 13

The following polyethylene oxide (7) was used as hydrophobic the polymeric membrane to form the intermediate layer. The degree of polymerization (m) was 10,000.

40% by weight of sodium tetraphenylborate and 60% by weight of polyethylene oxide were weighed, and mixed and dispersed in 10 ml of distilled water with stirring. The dispersion was dried to prepare the intermediate layer. Silver/silver tetraphenylborate was used for the inner electrode and a potassium ion-selective membrane was used as the ion-selective membrane.

EXAMPLE 14

The following polycarboxyethylene oxide (8) (m=10,000 and l=100) was used as the polymeric ion-conductor to form the intermediate layer. Silver/silver tetraphenylborate was used as the inner electrode and a potassium ion-selective membrane was used as the ion-selective membrane.

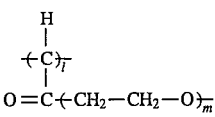

40% by weight of sodium tetraphenylborate and 60% by weight of polycarboxyethylene oxide were weighed, and mixed and dispersed in 10 ml of distilled water with stirring. The dispersion was dried to prepare the intermediate layer.

EXAMPLE 15

The following sodium polyacrylate (9) (l=100) was used as the polymeric ion-conductor to form the intermediate layer. Silver/silver tetraphenylborate was used as the inner electrode and a potassium ion-selective membrane was used as the ion-selective membrane.

40% by weight of sodium tetraphenylborate and 60% by weight of sodium polyacrylate were weighed, and mixed and dispersed in 10 ml of distilled water with stirring. The dispersion was dried to prepare the intermediate layer.

EXAMPLE 16

The following sodium polystyrenesulfonate (10) (l=100) was used as the polymeric ion-conductor to form the intermediate layer. Silver/silver tetraphenylborate was used as the inner electrode and a potassium ion-selective membrane was used as the ion-selective membrane.

40% by weight of sodium tetraphenylborate and 60% by weight of sodium polystyrenesulfonate were weighed, and mixed and dispersed in 10 ml of distilled water with stirring. The dispersion was dried to prepare the intermediate layer.

EXAMPLE 17

The following compound (11) (n=1000), namely, natural polymer cellbios in which the hydroxyl group of the hydroxymethyl group was substituted with a carboxylate was used as the polymeric ion-conductor to form the intermediate layer. Silver/silver tetraphenylborate was used as the inner electrode and a potassium ion-selective membrane was used as the ion-selective membrane.

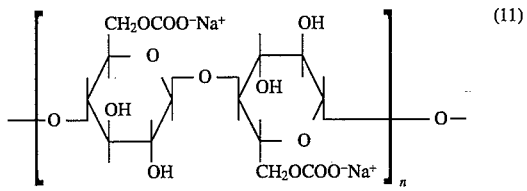

40% by weight of sodium tetraphenylborate and 60% by weight of the compound (11) were weighed, and mixed and dispersed in 10 ml of distilled water with stirring. The dispersion was dried to prepare the intermediate layer.

EXAMPLE 18

The following compound (12) (n=100), namely, natural polymer maltose in which the hydroxyl group of the hydroxymethyl group was substituted with a carboxylate was used as the polymeric ion-conductor to form the intermediate layer. Silver/silver tetraphenylborate was used as the inner electrode and a potassium ion-selective membrane was used as the ion-selective membrane.

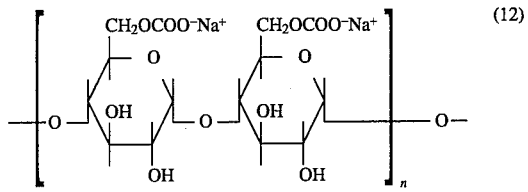

40% by weight of sodium tetraphenylborate and 60% by weight of the compound (12) were weighed, and mixed and dispersed in 10 ml of distilled water with stirring. The dispersion was dried to prepare the intermediate layer.

It is needless to say that as the inner electrode the metal/metal halogenide as explained in Example 12 can be used in place of the silver/silver tetraphenylborate in the above Examples 13–18.

Figure 15:
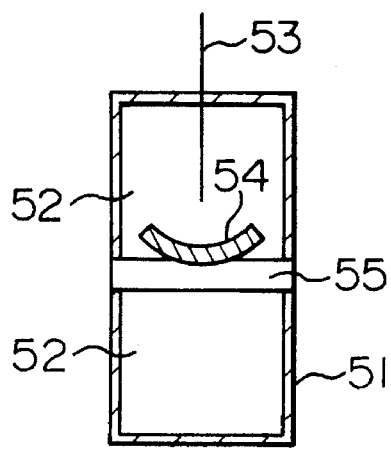
FIG. 15 is a sectional view of the conventional ion-selective electrode.

Next, the stability of the solid-state ion sensors of the Examples 12–18 will be explained in comparison with a conventional example. The conventional example was the ion-selective electrode as shown in FIG. 15. A potassium ion-selective membrane was used as the ion-selective membrane. The inner electrolyte solution was composed of agar (50% by weight), a supporting electrolyte (20% by weight) and water (30% by weight). The silver/silver chloride inner electrode was prepared in the following manner. Electrodeposition was carried out using a silver wire (0.5 mm in diameter×50 mm) pretreated with conc. nitric acid as an anode and a platinum wire (0.5 mm in diameter×50 mm) as a cathode in a potassium chloride solution (1 mM) by application of a voltage of about 0.7 V. After completion of the electrodeposition, the electrode was washed with water and dried to obtain a silver/silver chloride inner solid electrode.

COMPARATIVE EXAMPLE

Figure 12:
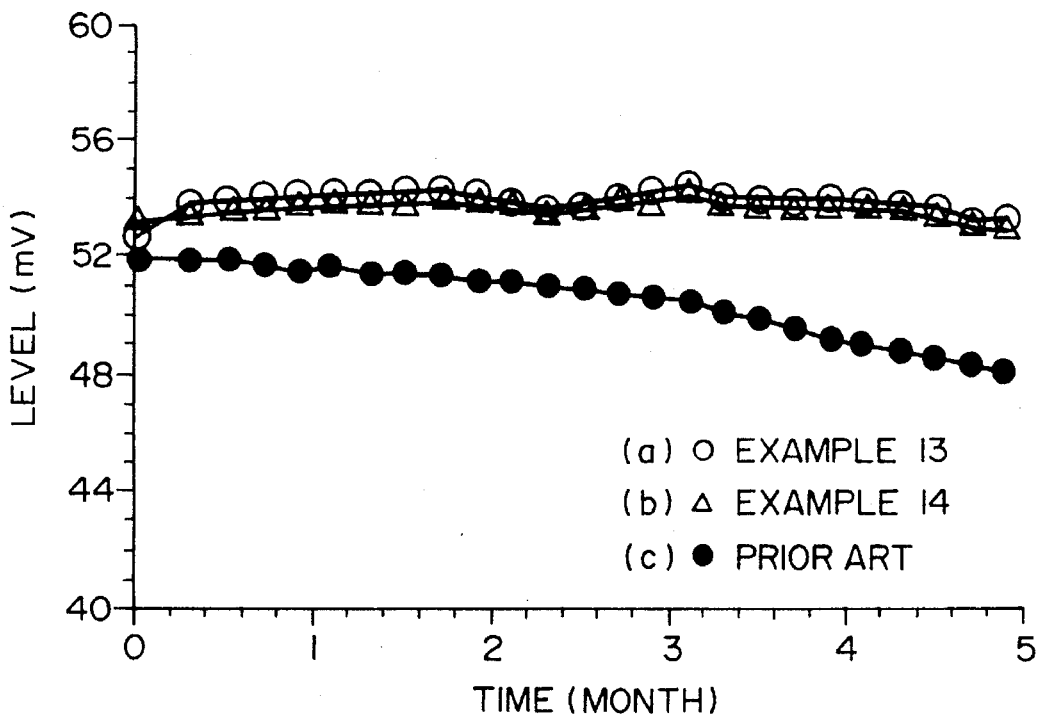
FIGS. 12, 13 and 14 are graphs which show the potential stability of the potassium ion sensor of the present invention.

FIG. 12 shows the changes of the electrode potential with time in determination of potassium ion in aqueous potassium chloride solution (concentration: 100 mmol/l) by the solid-state ion sensors of Examples 13 and 14 and the above conventional example. In FIG. 12, the curves (a), (b) and (c) show the results of Examples 13 and 14 and the conventional example, respectively. The solid-state ion sensor of the conventional example showed much decrease in the electrode potential while the solid-state ion sensors of the Examples of the present invention showed substantially no decrease in the electrode potential. The results indicate that the conducting action of the intermediate layer between the ion-selective membrane and the inner electrode is very stably maintained.

Figure 13:
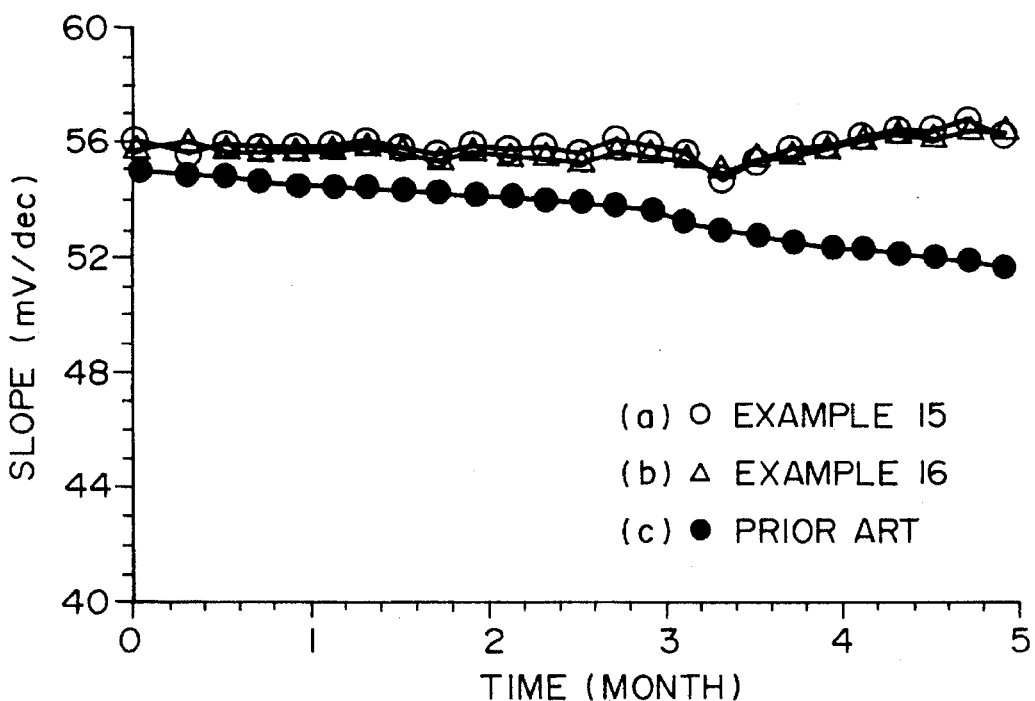

FIG. 13 shows the change of the slope with time in determination of potassium ion in aqueous potassium chloride solution (concentration: 100 mmol/l) by the solid-state ion sensors of Examples 15 and 16 and the above conventional example. In FIG. 13, the curves (a), (b) and (c) show the results of Examples 15 and 16 and the conventional example, respectively. The slope of the solid-state ion sensor of the conventional example was unstable and decreased in a relatively short time while that of the solid-state ion sensors of the Examples according to the present invention was stable as compared with that of the conventional example and was maintained at a high value for a long period of time.

Figure 14:
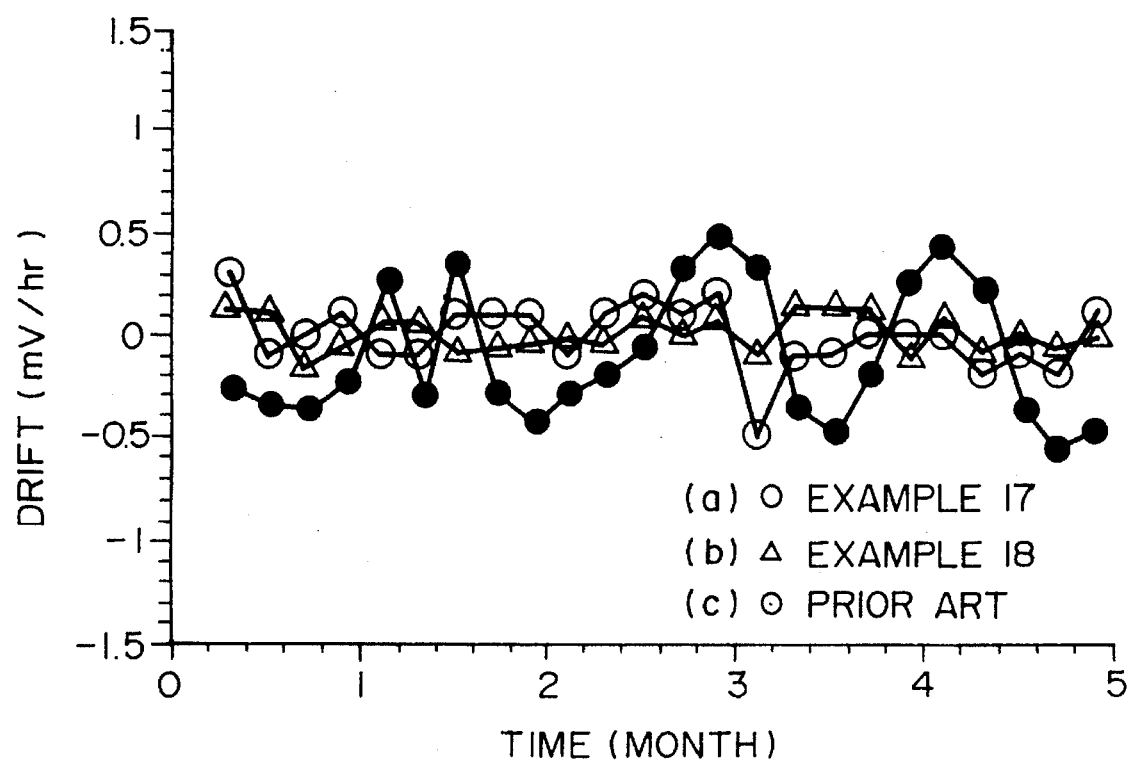

FIG. 14 shows the changes of the drift of the electrode potential with time in determination of potassium ion in aqueous potassium chloride solution (concentration: 100 mmol/l) by the solid-state ion sensors of Examples 17 and 18 and the above conventional example. In FIG. 14, the curves (a), (b) and (c) show the results of Examples 17 and 18 and the conventional example, respectively. The solid-state ion sensor of the conventional example was unstable in the electrode potential and showed a great drift while the solid-state ion sensors of the Examples of the present invention showed highly stable drift for a long period of time.

As explained above, the solid-state ion sensors of the present invention have the feature that the electrode performance is stably maintained for a long period of time as compared with that of the conventional example.

What is claimed is:

1. A flow-through cell for electrochemical measurement of an ion concentration in a sample solution, comprising:

a straight-flow path through which the sample solution flows;

an internal space separated from said straight flow path;

an ion-selective membrane having a curved portion projecting through an opening from said internal space into said straight flow path, the membrane separating said straight flow path from said internal space, and the curved portion of said ion-selective membrane providing a first surface projecting into said straight flow path;

an intermediate layer consisting essentially of a hydrophilic polymeric ion-conductor having an alkali metal salt able to dissociate and ionize and providing a first surface contacting a second surface of the ion-selective membrane in said internal space;

a metal/metal-salt electrode containing a second surface of the intermediate layer for detecting a potential of said ion-selective membrane;

an external terminal; and a conductive lead connecting said metal/metal-salt electrode to said external terminal.

2. A flow-through cell according to claim 1, wherein the polymeric ion-conductor comprises a polymer having a main chain containing carbon atoms and side chains bonding to the main chain, each of the side chains include a carboxylate ion or sulfonate ion and alkali metal ion binding to the carboxylate ion or sulfonate ion.

3. A flow-through cell according to claim 1, wherein the ion-selective membrane comprises a matrix, a plasticizer and an ion-selective material, the matrix is a polyvinyl chloride or silicone rubber, the plasticizer is selected from the group consisting of dioctyl adipate (DOA), dioctyl sebacate (DOS), tri(2-ethylhexyl)trimellitate (TOTM), ortho-nitrophenyloctyl ether (o-NPOE), tris(2-ethylhexyl)phosphate (TEHP) and n-tetradecyl alcohol (n-TDA), and the ion-selective material is selected from the group consisting of valinomycin, {bis(12-crown-4)methyl}-methyldodecylmalonic acid and quaternary ammonium salts.

4. A flow-through cell for electrochemical measurement of an ion concentration in a sample solution, comprising:

a straight flow path through which the sample solution flows;

an internal space separated from said straight flow path:

an ion-selective membrane having a curved portion projecting through an opening from said internal space into said straight flow path, the membrane separating said straight flow path from said internal space, and the curved portion of said ion-selective membrane providing a first surface projecting into said straight flow path;

an intermediate layer consisting essentially of a hydrophilic polymeric membrane having a dispersed hydrophilic electrolyte containing halogen ions, and the intermediate layer providing a first surface contacting a second surface of the ion-selective membrane in said internal space;

a metal/metal-salt electrode contacting a second surface of the intermediate layer for detecting a potential of said ion-selective membrane;

an external terminal; and a conductive lead connecting said metal/metal salt electrode to said external terminal.

5. A flow-through cell according to claim 4, wherein the electrolyte is greater than 1% of the hydrophilic polymer by weight.

6. A flow-through cell according to claim 4, wherein the hydrophilic polymer is selected from the group consisting of polyvinyl alcohol, agarose, polyacrylamide, and polyethylene oxide.

7. A flow-through cell according to claim 4 wherein the ion-selective membrane comprises a matrix, a plasticizer and an ion-selective material, the matrix is polyvinyl chloride or silicone rubber, the plasticizer is selected from the group consisting of dioctyl adipate (DOA), dioctyl sebacate (DOS), tri(2-ethylhexyl)trimellitate (TOTM), ortho-nitrophenyloctyl ether (o-NPOE), tris(2-ethylhexyl)phosphate (TEHP) and n-tetradecyl alcohol (n-TDA), and the ion-selective material is selected from the group consisting of valinomycin, {bis(12-crown-4)methyl}-methyldodecylmalonic acid and quaternary ammonium salts.

* * * * *